United States Patent [19]

Hall et al.

[11] Patent Number: 5,349,435
[45] Date of Patent: Sep. 20, 1994

[54] MACHINE FOR INSPECTING THE BOTTOM OF GLASS CONTAINERS

[75] Inventors: Benjamin L. Hall, Corning; Leo B. Baldwin, Horseheads, both of N.Y.

[73] Assignee: Emhart Glass Machinery Investments Inc., Wilmington, Del.

[21] Appl. No.: 73,700

[22] Filed: Jun. 8, 1993

[51] Int. Cl.$^5$ .................. G01N 21/90; G01N 9/04
[52] U.S. Cl. .................. 356/240; 356/428; 250/223 B
[58] Field of Search .................. 356/240, 428; 250/223 B; 209/524, 526, 528

[56] References Cited

U.S. PATENT DOCUMENTS

| | | | |
|---|---|---|---|
| 4,448,526 | 5/1984 | Miyazawa | 356/240 |
| 4,943,713 | 7/1990 | Yoshida | 356/240 |
| 5,095,204 | 3/1992 | Novini | 356/240 |
| 5,216,239 | 6/1993 | Yoshida | 250/223 B |
| 5,280,170 | 1/1994 | Baldwin | 356/240 |

Primary Examiner—Rolf Hille
Assistant Examiner—Minhloan Tran
Attorney, Agent, or Firm—Spencer T. Smith

[57] ABSTRACT

A machine for inspecting the bottom of a glass container having an opening at the top thereof comprising means for delivering a glass container to an inspection station, the inspection station including a two dimensional camera having an imaging surface for viewing the bottom of the glass container through the opening of the bottle, a light source for directing light through the bottom of the container towards the imaging surface, a computer for evaluating the viewed bottom imaged on the imaging surface, and means for reducing the dynamic brightness range for the viewed bottom image including a spatial modulator located between the imaging surface and the light source and the computer complimenting and transferring the image of the glass container on the imaging surface to the spatial light modulator.

5 Claims, 2 Drawing Sheets

MACHINE FOR INSPECTING THE BOTTOM OF GLASS CONTAINERS

BACKGROUND OF THE INVENTION

The present invention relates to the inspection of glass bottles to identify flaws in the bottom of the bottles. A diffused light source directs light upwardly through the bottom of the bottle and a two dimensional camera looks at the illuminated bottom through the bottle mouth to see any defect.

A glass bottle may have a wide disparity of thicknesses in the base. A glass bottle may, for example, have a heavy heel portion. As a result, the camera will see varying light intensities and may not see enough light in the heel region to see the defects. To see these defects, the intensity of the light must be increased but the intensity level of the light passing through the thin portions may present a dynamic brightness range (contrast ratio) beyond the capabilities of the camera. This dynamic brightness range can be reduced by matching the spectral composition of the light to the spectral absorption of the bottle glass by passing the light through a colored filter matching the color of the bottle.

When spectral matching of the light source to the bottle does not sufficiently reduce the contrast ratio to fall within the dynamic brightness range of the camera, spot or ring filters designed for the application may be applied to overlay the light source to attenuate the light from the backlight source in a pattern which corresponds to those areas of the bottle which are transmitting too much light and overloading the sensor in the corresponding image regions.

SUMMARY OF THE INVENTION

It is accordingly an object of the present invention to provide an improved device for attenuating the light from the backlight source to reduce the contrast ratio.

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE DRAWINGS

Referring to the drawing.

DETAILED DESCRIPTION OF PREFERRED EMBODIMENTS

Figure 1:
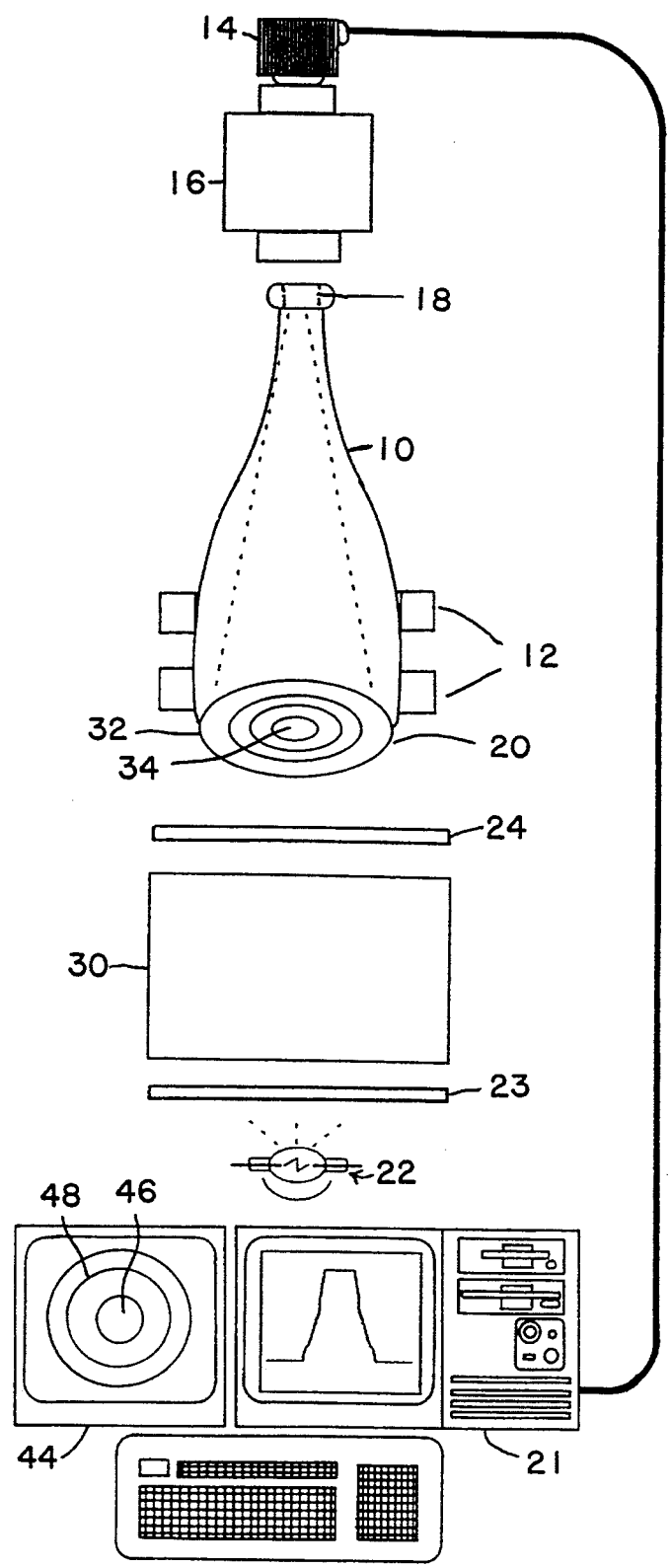
FIG. 1 is an oblique schematic showing of the bottom inspection device made in accordance with the teachings of the present invention with the spatial modulator off.

A bottle 10 which is being conventionally displaced at a constant speed by opposed pairs of belts 12, passes through a bottom inspection station where an image is sensed on the imaging surface of a two dimensional camera 14 looking through a lens 16 and through the opening 18 of the bottle at the bottom 20 of the bottle. This data is evaluated by a computer 21.

A high quality diffuse backlight is provided using a point source 22 (here an arc or gas discharge lamp which provides a white light which will be strobed), a collimating lens 23 (a Fresnel lens) and a non-Lambertian diffusing element 24. This diffused light is uniform in brightness over the entire surface of the diffusing element, and the variation in brightness with angle is uniform over the entire surface. This source will work well with most bottles and lenses, however, wide angle lenses positioned near the source (as with a wide bottom short bottle) will see the light level fall off toward the edges of the light source. This effect will compound the problem of viewing a colored bottle with a relatively thicker heel section.

A spatial modulator in the form of a flat panel liquid crystal display 30 which is operated by the computer 21 is located between the collimating lens 23 and the diffuser 24. Such a spatial modulator is capable of high spatial resolution (typically 307,200 individual addressable regions of modulation, high dynamic resolution (64 different levels of resolution) and wide dynamic range (typically 10:1). The size is also appropriate at 8" to 10" diagonal. By locating the spatial modulator between the collimating lens and the diffusing element any fine structure of the modulator would be blended by the diffuser. If the fine structure is not a problem, the modulator can be located after the diffuser or can be used in place of the diffuser. The display 30 could be a color display with spectrally selective variable attenuation light gates so that the color of the container could be matched.

Figure 2:
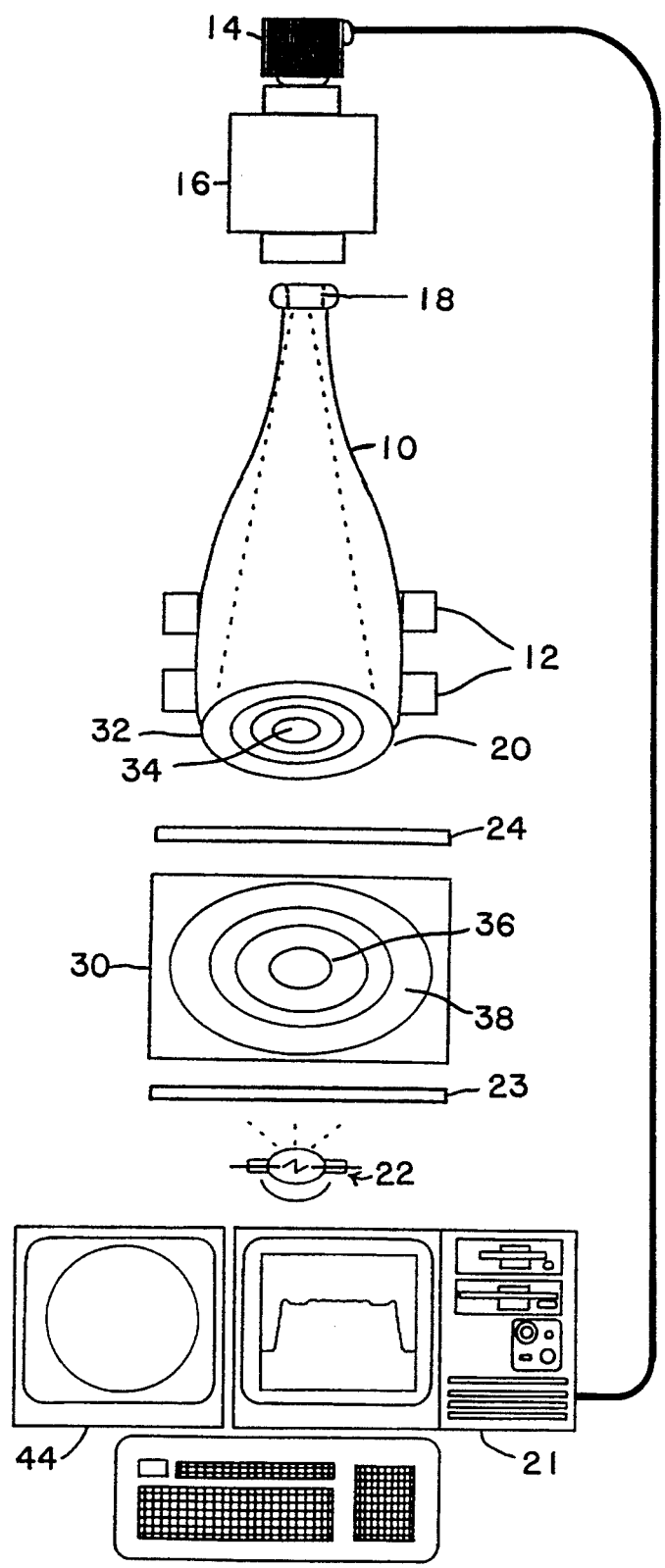
FIG. 2 is a view similar to the view of FIG. 1 with the spatial modulator operational.

In the first embodiment a picture of the bottle bottom 20 is taken with no modulation and mid-range transmittance (FIG. 1). The image of the bottom 20 of the bottle which has a thick annular heel portion 32 and a thin central portion 34 which, as shown on the monitor 44, could have a bright inner circle 46 where the glass is thin and a darker outer ring 48 where the glass is thick, is complimented and transferred to the spatial light modulator (FIG. 2) where it in effect defines a filter having a dark central zone 36 and a neutral outer annular ring portion 38. The transformed image is the same size and concentric to the bottle bottom as seen by the camera and as a result the camera will image a bottle bottom having a uniform intensity (the bottle bottom is shown as in FIG. 1). This process, if not immediately effective to achieve the desired uniform image intensity, could be repeated, with the complimentary bottle image added to the bottom light image until an optimal image of the bottle bottom is obtained. This complimented image would be applied to every bottle inspected. The dynamic image 47 along one scan line is shown on another monitor to show how the spatial modulator effectively defines a uniform intensity across the bottom of the bottle.

In the alternate embodiment, this complimented image forms the baseline of an adaptive per bottle process whereby every bottle is imaged twice—once with the baseline modulator image and again with optimized modulator image based on the first image. The second image would be analyzed for defects.

We claim:

1. A machine for inspecting the bottom of a glass container having an opening at the top thereof comprising means for delivering a glass container to an inspection station, said inspection station including a two dimensional camera having an imaging surface viewing the bottom of the glass container through the opening thereof, a light source for directing light through the bottom of the container towards said imaging surface, a computer for evaluating the viewed bottom imaged on said imaging surface, and means for reducing the dynamic brightness range for the viewed bottom image including a spatial modulator located between said imaging surface and said light directing means and said computer further comprising means for complimenting and transferring the image of the viewed bottom to said spatial light modulator so that the viewed bottom of a container to be inspected at the inspection station and the complimented image will be imaged concentrically and the same size on said imaging surface.

2. A machine for inspecting the bottom of a glass container according to claim 1, further comprising
means for collimating light from said light source and directing said collimated light towards said imaging surface, said collimating means located between said light source and said spatial modulator.

3. A machine for inspecting the bottom of a glass container according to claim 2, further comprising
means for diffusing said collimated light, said diffusing means located between said imaging surface and said spatial modulator.

4. A machine for inspecting the bottom of a glass container according to claim 1, wherein said spatial modulator comprises a flat panel liquid crystal display.

5. A machine for inspecting the bottom of a glass container according to claim 1, wherein said spatial modulator comprises a color flat panel liquid crystal display.

* * * * *